(12) United States Patent
Seal et al.

(10) Patent No.: US 6,309,069 B1
(45) Date of Patent: Oct. 30, 2001

(54) PERSONAL IDENTIFICATION

(75) Inventors: Christopher H Seal, Woodbridge; Maurice M Gifford; David J McCartney, both of Ipswich, all of (GB)

(73) Assignee: British Telecommunications public limited company, London (GB)

(*) Notice: Subject to any disclaimer, the term of this patent is extended or adjusted under 35 U.S.C. 154(b) by 0 days.

(21) Appl. No.: 09/194,319

(22) PCT Filed: Jun. 6, 1997

(86) PCT No.: PCT/GB97/01526

§ 371 Date: Nov. 24, 1998

§ 102(e) Date: Nov. 24, 1998

(87) PCT Pub. No.: WO97/46980

PCT Pub. Date: Dec. 11, 1997

(30) Foreign Application Priority Data

| Jun. 6, 1996 | (GB) | 961787 |
| Oct. 18, 1996 | (GB) | 962900 |
| Apr. 15, 1997 | (EP) | 9732580 |

(51) Int. Cl.[7] ................................................. A61B 3/10
(52) U.S. Cl. ............................................................ 351/221
(58) Field of Search ............................. 600/318, 319; 396/51; 351/208, 209, 210, 211, 212, 221

(56) References Cited

U.S. PATENT DOCUMENTS

| 4,109,237 | 8/1978 | Hill . |
| 4,256,384 | 3/1981 | Kani et al. . |
| 4,266,861 | 5/1981 | Sawa . |
| 4,394,074 | 7/1983 | McMahon et al. . |
| 4,533,222 | 8/1985 | Ishikawa . |

(List continued on next page.)

FOREIGN PATENT DOCUMENTS

| 0061832 A2 | 10/1982 | (EP) . |
| 0534477 A1 | 9/1992 | (EP) . |
| 2461481 | 2/1981 | (FR) . |
| 2516778 | 5/1983 | (FR) . |
| 2521851 | 8/1983 | (FR) . |
| 2604080 | 9/1986 | (FR) . |

(List continued on next page.)

OTHER PUBLICATIONS

Japanese Giant Spends US $25.8M on Iris Scanning Technology, Biometric Technology Today, vol. 3, No. 6, Oct. 1995.

Cope, The Corneal Polarisation Cross, J. Opt. Soc. of America, vol. 68, No. 8, pp. 1139–1140, 1978.

Robbins, Biological Perspectives on Human Pigmentation, pp. 74–75, 1991.

Radke, Auf einem Blick, Funkschau, vol. 59, No. 1, Jan. 1987, Munchen.

Industrial Cryptography, IEE Review, May 1996—sales brochure.

(List continued on next page.)

Primary Examiner—George Manuel
(74) Attorney, Agent, or Firm—Nixon & Vanderhye P.C.

(57) ABSTRACT

An optical apparatus records light reflected from one or more of a user's facial features. While the image is captured, visible light from a display or other scene to be viewed by the user passes to the user's eye. A portable iris pattern capture device is used. Near-infrared light is directed towards the user's eye from where it is reflected back into the apparatus. Visible light from an LCD display mounted at the rear of the apparatus travels out to the user's eye from the apparatus. A hot mirror inside the apparatus directs the near-infrared light reflected from the user's eye to a camera unit, and does not significantly attenuate the visible light emanating from the display.

21 Claims, 5 Drawing Sheets

U.S. PATENT DOCUMENTS

| | | |
|---|---|---|
| 4,620,318 | 10/1986 | Hill . |
| 4,755,043 | 7/1988 | Carter . |
| 4,786,142 | 11/1988 | Karecki . |
| 4,821,118 | 4/1989 | Lafreniere . |
| 4,834,528 | 5/1989 | Howland et al. . |
| 4,993,068 | 2/1991 | Piosenka et al. . |
| 5,118,179 | 6/1992 | Sano et al. . |
| 5,214,454 | 5/1993 | Sano . |
| 5,291,560 | 3/1994 | Daugman . |
| 5,359,669 | 10/1994 | Shanley et al. . |
| 5,433,197 * | 7/1995 | Stark ................................. 600/319 |
| 5,485,241 * | 1/1996 | Irie et al. ............................. 396/51 |
| 5,572,596 | 11/1996 | Wildes et al. . |
| 5,576,796 * | 11/1996 | Akashi ................................ 396/51 |

FOREIGN PATENT DOCUMENTS

| | | |
|---|---|---|
| 2627074 | 2/1988 | (FR) . |
| 2630365 | 4/1988 | (FR) . |
| 2690329 | 4/1992 | (FR) . |
| 2119941A | 11/1983 | (GB) . |
| 2201801A | 9/1988 | (GB) . |
| WO 89/04139 | 5/1989 | (WO) . |
| WO 92/05736 | 4/1992 | (WO) . |
| WO 94/09446 | 4/1994 | (WO) . |
| WO 94/10900 | 5/1994 | (WO) . |
| WO 96/07978 | 3/1996 | (WO) . |
| WO 97/05578 | 2/1997 | (WO) . |

OTHER PUBLICATIONS

Daugman, "High Confidence Visual Recognition of Persons by a Test of Statistical Independence", IEEE Transactions of Pattern Analysis and Machine Intelligence, vol. 15, No. 11, Nov. 1993.

Collection of web–pages from Identification Technologies International, 1997.

Web–page describing Sensar Inc.'s "I risident" system, 1997.

Karla Harby, "A Discerning Eye", p. 29, Scientific American, Apr. 1996.

Anjana Ahuja, "A Peep into the Future of Iris ID", The Times, Apr. 14, 1996.

* cited by examiner

PERSONAL IDENTIFICATION

RELATED APPLICATIONS

This application is related to the following co-pending commonly assigned applications:

1. McCartney et al "Imaging Apparatus", Ser. No. 09/180, 760 filed Nov. 13, 1998.
2. Seal et al, "Personal Identification", Ser. No. 09/194, 318 filed Nov. 24, 1998.
3. Seal et al, "Personal Identification", Ser. No. 09/194, 737 filed Dec. 2, 1998.

BACKGROUND OF THE INVENTION

1. Field of the Invention

The present invention relates to apparatus for and methods of personal identification. It has particular utility in relation to apparatuses which are required to capture an image of anterior features of an eye and display an image to the eye simultaneously. Such an apparatus might be used in an authentication device which captures an image of an iris of a user.

2. Related Art

Apparatuses for capturing an image of a persons' eye at the same time as providing a display for viewing by the person's eye are known. For example, IriScan Inc. market a System 2000EAC™ authentication apparatus. Another example is the pupillometer apparatus disclosed in international patent application WO 92/05736.

The former apparatus comprises an iris pattern capture unit and an identification code generation unit. The iris pattern capture unit has a housing having two apertures. An infra-red illumination source is arranged to project visible and infra-red light through the first aperture to illuminate a person's eye. A camera, installed within the apparatus is arranged such that its field of view is through the second aperture. In using the apparatus the person looks through the second aperture at a display which reproduces the image seen by the camera. At the same time, light from the illumination source is reflected from the person's eye through the second aperture towards the camera. The display enables the person to position his eye such that it is in focus and located in the centre of the field of view of the camera.

In practice it is found that the user must position his or her eye within a narrow range of distances from the device in order for a successful capture of an image of the user's eye to be achieved.

A fovea-centred eye fundus scanner is disclosed in European Patent Application 0 126 549. Because the apparatus uses scanning optics to examine the fundus (retina and choroid) of an eye, it is complex and bulky.

SUMMARY OF THE INVENTION

These are two of the problems addressed by the present invention, which provides an apparatus for providing an information signal characteristic of an eye, said apparatus comprising:

a housing having an entrance window;

an illumination source mounted on the housing, and operable to illuminate the eye over an area outside the pupil; and an image capture device mounted within the housing, in optical communication with said entrance window, and operable to provide an image signal representing one or more features of the anterior of the eye responsive to the incidence of light from the illumination source reflected from the eye;

an optical device;

wherein, in use, visible light travels along a first optical path via the optical device to the eye to provide a visible image to be viewed by the eye and light from the illumination source and reflected from the eye travels along a second optical path via the optical device to said image capture apparatus;

wherein said optical device is arranged to interact with at least one of said illumination light and said visible light such that substantially all illumination light of a predetermined type travels further along said second optical path towards said image capture apparatus, and a significant proportion of said visible light travels further along said first optical path towards the eye.

The terms 'optical' and 'light' as used herein relate to electromagnetic radiation in the infra-red, visible and ultra-violet portions of the electromagnetic spectrum, i.e. having wavelengths in the range 10 nm to 1 mm.

Because most of the illumination light of the predetermined type arrives at the image capture apparatus, the present invention achieves a number of advantages.

Firstly, since more light is received at the image capture apparatus, the aperture of the optical arrangement associated with it can be reduced. This has the result that the depth of focus of the image capture apparatus is increased. Thus, the constraints placed on where the eye must be positioned in relation to the apparatus in order to provide a satisfactorily focused image are relaxed.

Secondly, the time of exposure may be reduced, thereby reducing the need for the person to remain still whilst the image is captured.

Thirdly, the present invention also allows a satisfactory image to be captured in situations where less light to which the image capturing apparatus is responsive is available. This is beneficial since safety considerations limit the light that can directed towards the eye. It is also useful in reducing the power requirement of the apparatus, this being a particular advantageous in relation to portable equipment powered by batteries.

Those skilled in the art will realise that the above advantages could be realised individually or in combination. Generally, providing more light to an image capture apparatus improves the quality of the resultant image.

Any increase in the proportion of said user light of a predetermined type which is incident upon the image capture apparatus (in comparison to known apparatuses) leads to some improvement in performance. However, it is preferred that more than 75% of the user light of a predetermined type travels further along the optical path towards the image capture apparatus.

In addition to the above, allowing the visible light to pass substantially unattenuated towards the user increases the apparent brightness of the display. This means that the amount of power consumed by the apparatus is reduced; a particularly useful feature in portable apparatuses. It is preferred that more than 75% of the visible light travels further along the optical path towards the user.

The anterior feature of the eye might be the iris, cornea, sclera, or eyelids or a comnbination of two or more of these.

The apparatus may be adapted to be brought by the user to his own eye or to the eye of another person or animal. Alternatively, the apparatus may be fixed in place, requiring the person whose eye is being investigated to align his head accordingly.

In some cases, the visible image seen by the eye might simply be a view through the apparatus. In others, a display means provides the visible image or overlays a partial display on that already present to provide the visible image. This has the advantage that information can be provided to the eye at the time of use of the apparatus. Looked at another way, the user image capture unit can be operated whilst the eye is viewing information on the display.

One example of the use of a display involves the provision of an display which shows the image being received by the image capture apparatus. This is advantageous since it allows the person to move his head in order to improve the quality of the image captured.

In preferred embodiments the visible light directed towards the eye and the light directed towards the image capture apparatus have different spectra. This does not mean that the light directed towards the image capture apparatus necessarily lies outside the visible region of the electromagnetic spectrum. For example, the display might be created using red, blue and green LEDs which emit light in narrow spectral bands, the image capture apparatus receiving visible light which falls outside those bands but within the visible portion of the electromagnetic spectrum.

In advantageous versions of those embodiments the optical device comprises a wavelength selective reflector effective to reflect either said visible light or said light of a different spectrum, and to allow the passage of the other. Such reflectors are economical and their use allows the components of the apparatus to be conveniently located. The selectivity can, for example, be achieved using metallic coatings or coatings of dielectric material(s).

Since the illumination light is incident upon the eye, the apparatus is more comfortable in use if the predetermined type of light substantially consists of non-visible light.

Preferably, the predetermined type of light substantially consists of near infra-red light (i.e. having a wavelength between 700 nm and 3 μm). This is preferable because only unusually hot objects will emit significant amounts of light in that region of the electromagnetic spectrum, and thereby cause distortion of the image.

Further advantages are obtained when the optical device comprises a 'hot mirror'. A hot mirror is a device which is operable to reflect substantially all infra-red light whilst allowing the passage of visible light. It will be realised by those skilled in the art that a 'cold mirror' (which reflects substantially all visible light and allows the passage of infra-red light) could equally be used.

An advantage of using an illumination source is that both the spectrum and direction of the light used in forming the image can be controlled.

Particularly useful embodiments arise when the apparatus is designed to capture an image of an iris. The light impinging on the eye can be non-visible, making the apparatus comfortable in use. Furthermore, the intensity of the illumination light may be reduced owing to the increased amount of light incident on the image capture apparatus. Again, this makes the apparatus more comfortable in use.

In some embodiments the apparatus is arranged to be carried into an operative position by a user and further comprises a transmission device operable to transmit said information signal derived from said image signal to a remote apparatus. The transmission device might be a cordless transmission device providing infra-red, ultrasonic or RF communication with the remote apparatus. The use of the optical device in this case is particularly advantageous since the power requirements of the apparatus are reduced.

BRIEF DESCRIPTION OF THE DRAWINGS

Specific embodiments of the present invention will now be described, by way of example only, with reference to the accompanying figures, in which.

DETAILED DESCRIPTION OF EXEMPLARY EMBODIMENTS

Figure 1:
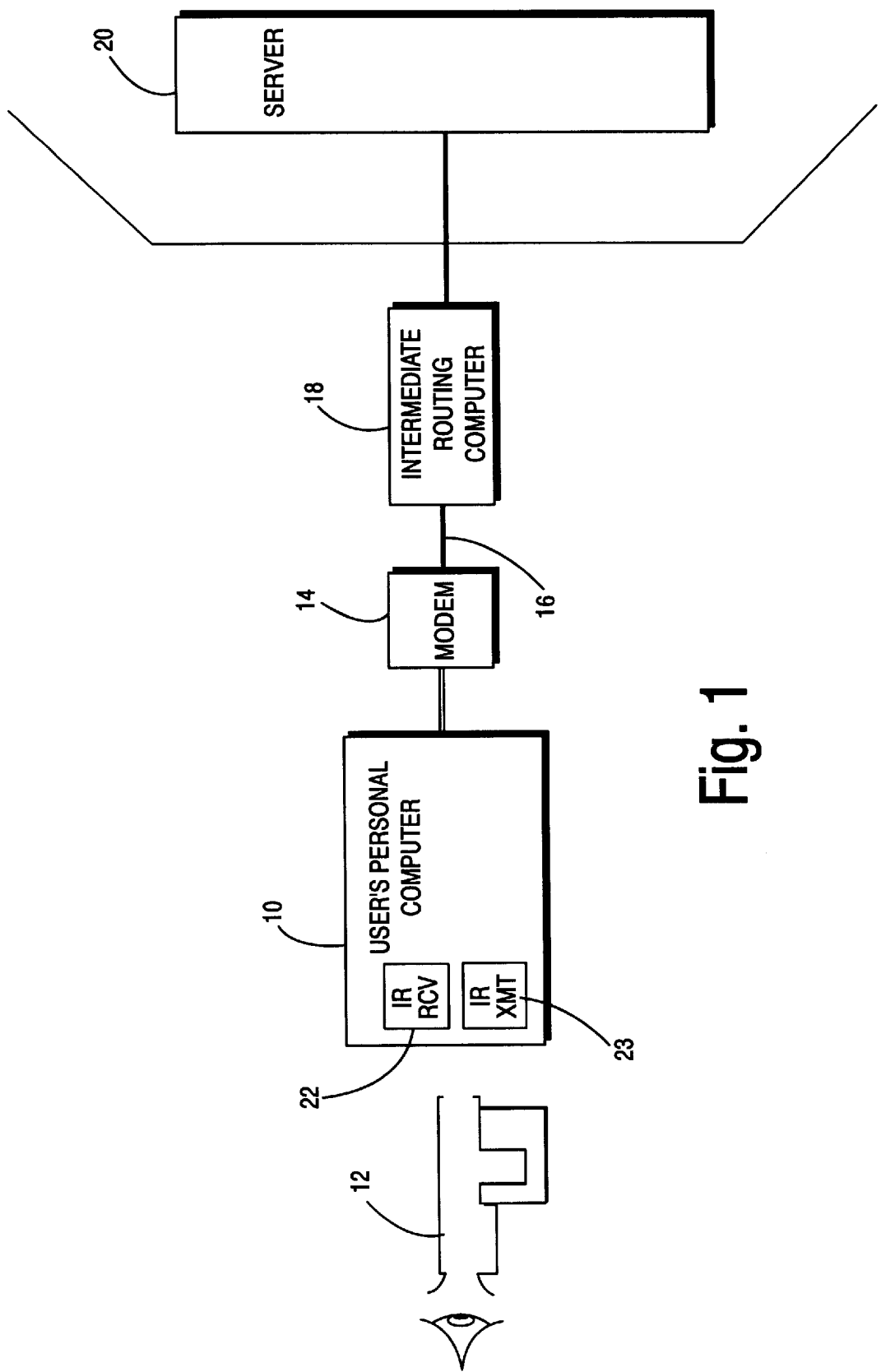
FIG. 1 illustrates a personal computer arranged for remote access to a shared computer.

FIG. 1 shows a user's personal computer (PC) 10 which, in addition to normal input/output devices and associated interfaces, has an infra-red receiver 22 and transmitter 23 and an infra-red signal interface card (not shown). These additional components enable communication of data between the user's PC 10 and an image capture apparatus 12.

The user's PC 10 is connected via a modem 14 and a telecommunications line 16 to an intermediate routing computer 18, which routes signals from the user's PC 10 to a server 20. The server 20 may, for example, belong to a corporation and have storage means containing files which are of significant value to that corporation. However, where the user of the PC 10 is an employee of that corporation, then the provision of a communications link between the PC 10 and the server 20 has the benefit of allowing that employee to work from home.

Figure 2:
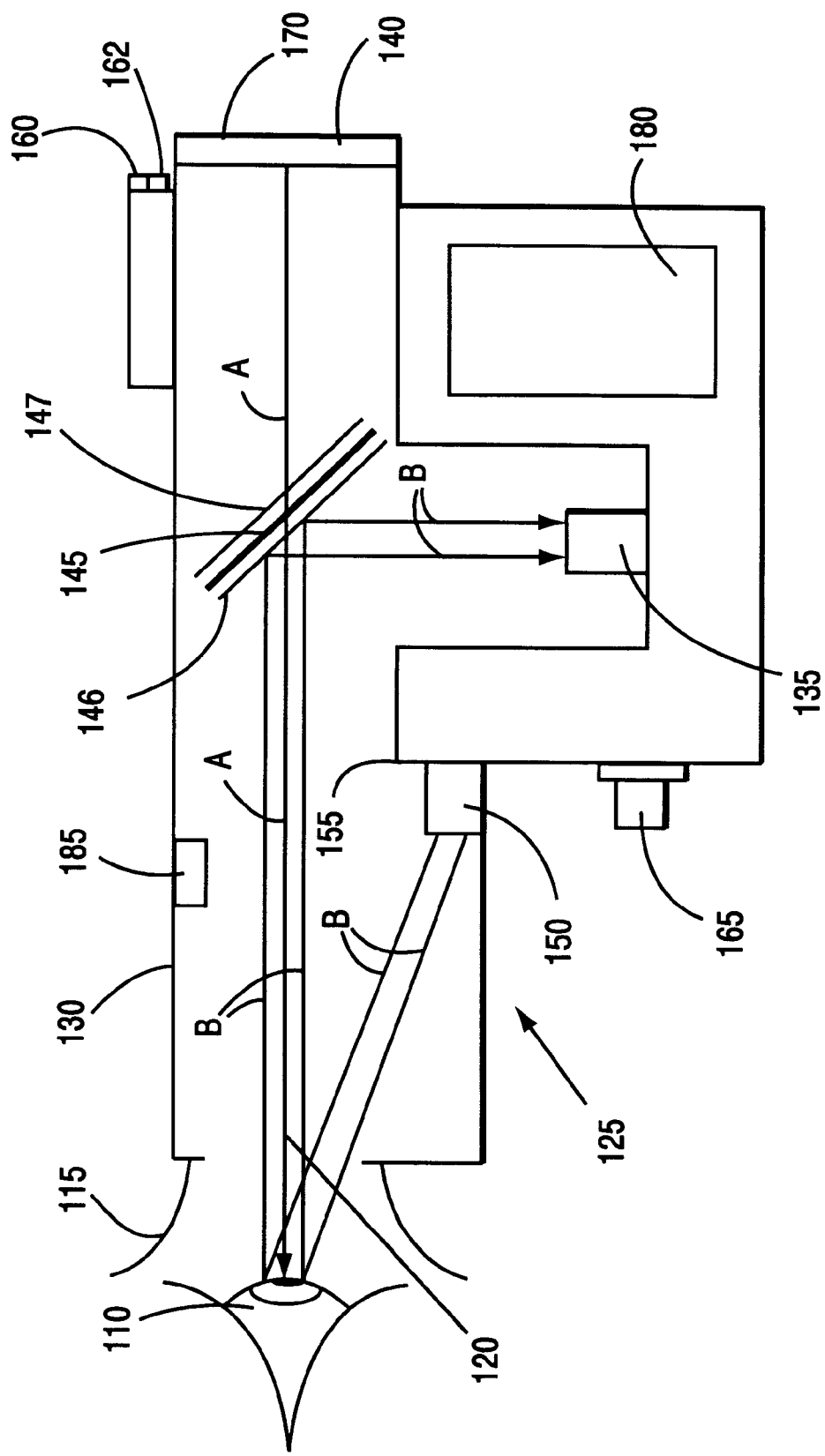
FIG. 2 is a schematic representation of an iris imaging apparatus.

FIG. 2 illustrates the image capture apparatus in more detail. The apparatus has a housing 125 which is generally T-shaped having an elongate horizontal barrel section 130 and a handle section which depends downwardly from the barrel 130 from a position intermediate its ends. The handle section is substantially hollow and is closed at its lowermost end. A charge coupled device (CCD) camera 135 is located at the base of the interior of the handle section. The camera is a black and white camera approximately equally sensitive to visible and near infra-red light. Connections (not shown) are provided from the output of the CCD camera 135 to a rearwardly facing liquid-crystal display (LCD) 170 mounted on the inside of the front end of the barrel 130. The handle portion also includes appropriate electronic circuitry 180 contained in the housing (described in more detail in relation to FIG. 2).

A window 120 is formed in the rearward end of the barrel 130. An eye-cup 115 is attached to the rearward end of the barrel and surrounds the window 120. The eye-cup 115 acts both as a means of minimising the amount of ambient light entering the apparatus and as the means for aligning the user's eye with the window 120.

A 'hot mirror' 145 (for example, as sold under catalogue number 35-6681 by Ealing Optics of Greylaine Rd, Watford, U.K.) is located directly above the CCD camera 135. The mirror 145 slopes downwardly and forwardly at 45° to the longitudinal axis of the barrel 130. The mirror is formed from a glass slide having a coating of dielectric materials on its underside. The other side of the glass slide is coated with an anti-reflective coating 147. The coating 146 of dielectric material is effective to reflect approximately 80% of near infra-red light which falls upon it and to allow the passage of approximately 90% of visible light which falls upon it.

A near infra-red light-emitting diode (LED) 150 is located on the inside of the barrel 130 between the mirror 145 and the eye-cup 115 and is operable to illuminate the user's eye. The source is mounted on the rearward facing side of a screen 155 to prevent light travelling directly from the source 150, via the mirror 145, to the camera 135. The barrel 130 also carries an internally-mounted optical indicator 185 comprising a red and a green LED positioned so as to be in the field of view of the user.

An infra-red (IR) transmitter 160 and receiver 162 are located on the front of the housing 125, in line with the longitudinal axis of the barrel 130, and a trigger button 165 is included on the handle portion operable by the user to control when the image is captured and/or transmitted to the user's PC 10.

The overall size of the apparatus depends mainly on the size of the opening for the eye 120 and on the level of comfort and ease of use required by a user of the apparatus. The hardware for the apparatus is designed onto a single ASIC chip, the size of which is not a limiting factor to the size of the apparatus. Also, known CCD cameras can have dimensions in the order of millimetres (or tens of millimetres if the size of the printed circuit board mounting is taken into consideration) and are not a limiting factor of the apparatus size.

Figure 3:
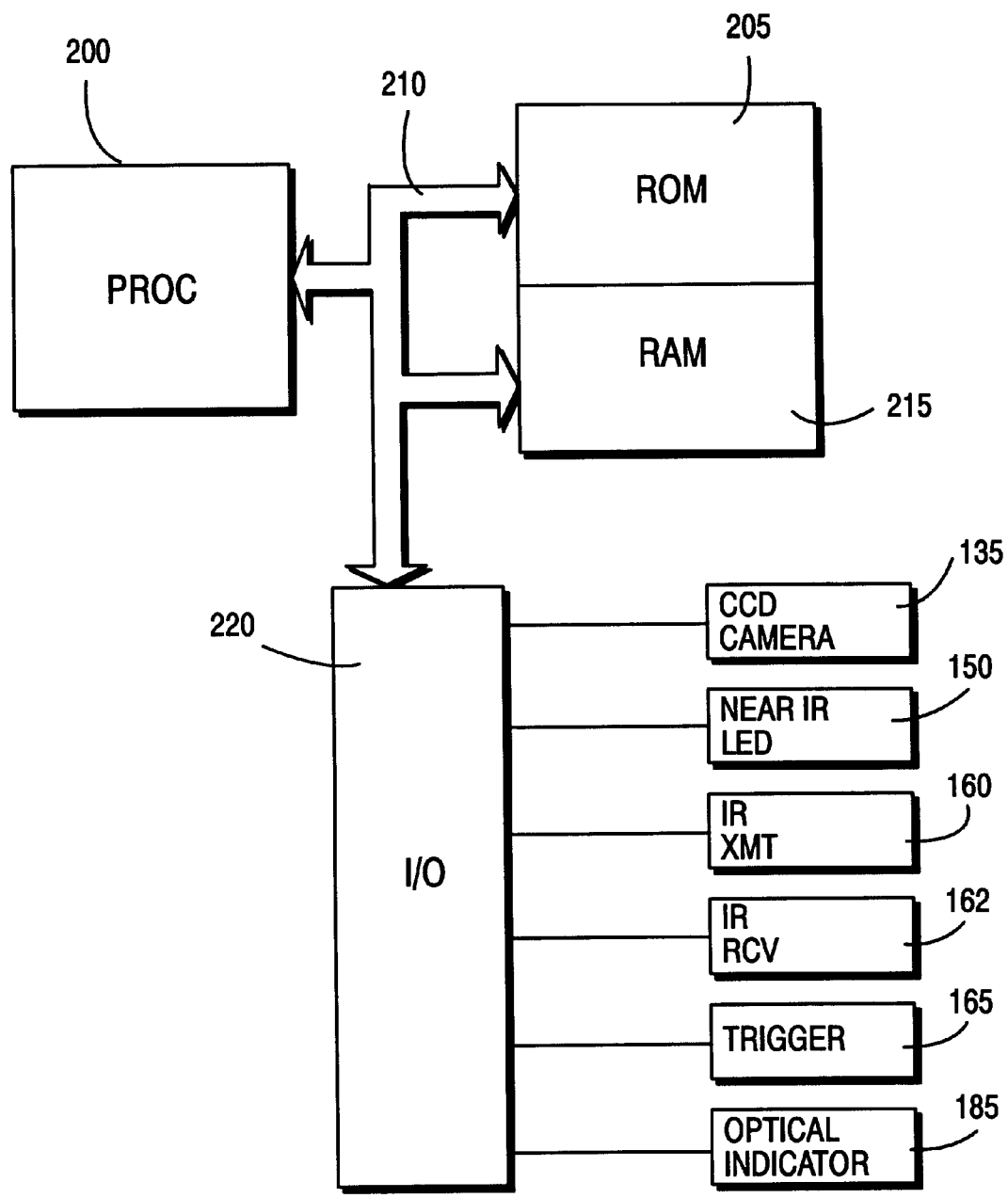
FIG. 3 is a schematic diagram which illustrates one possible hardware architecture for the imaging apparatus.

FIG. 3 shows one possible hardware architecture arrangement for the apparatus. As already stated, the processing hardware is preferably engineered onto a single application specific integrated circuit (ASIC). The apparatus is controlled by a processor 200 which runs software held in ROM 205. The processor 200 is connected via a bus 210 to the ROM 205, a block of RAM 215 and an input/output (I/O) controller 220. The RAM is large enough to hold at least one captured image of an eye. The I/O controller 220 is connected by appropriate circuitry and drivers (not shown) to the IR transmitter 160 and receiver 162, the CCD camera 135, the trigger 165, the near infra-red LED 150 and the optical indicator 185. The whole apparatus is powered by a suitable battery (not shown).

The processor 200 is sensitive to signals received from the trigger 165, the IR receiver 162 and the CCD camera 135. Also, the processor controls the IR transmitter 160, the near infra-red LED 150, the CCD camera operation and the optical indicator 185.

Figure 4:
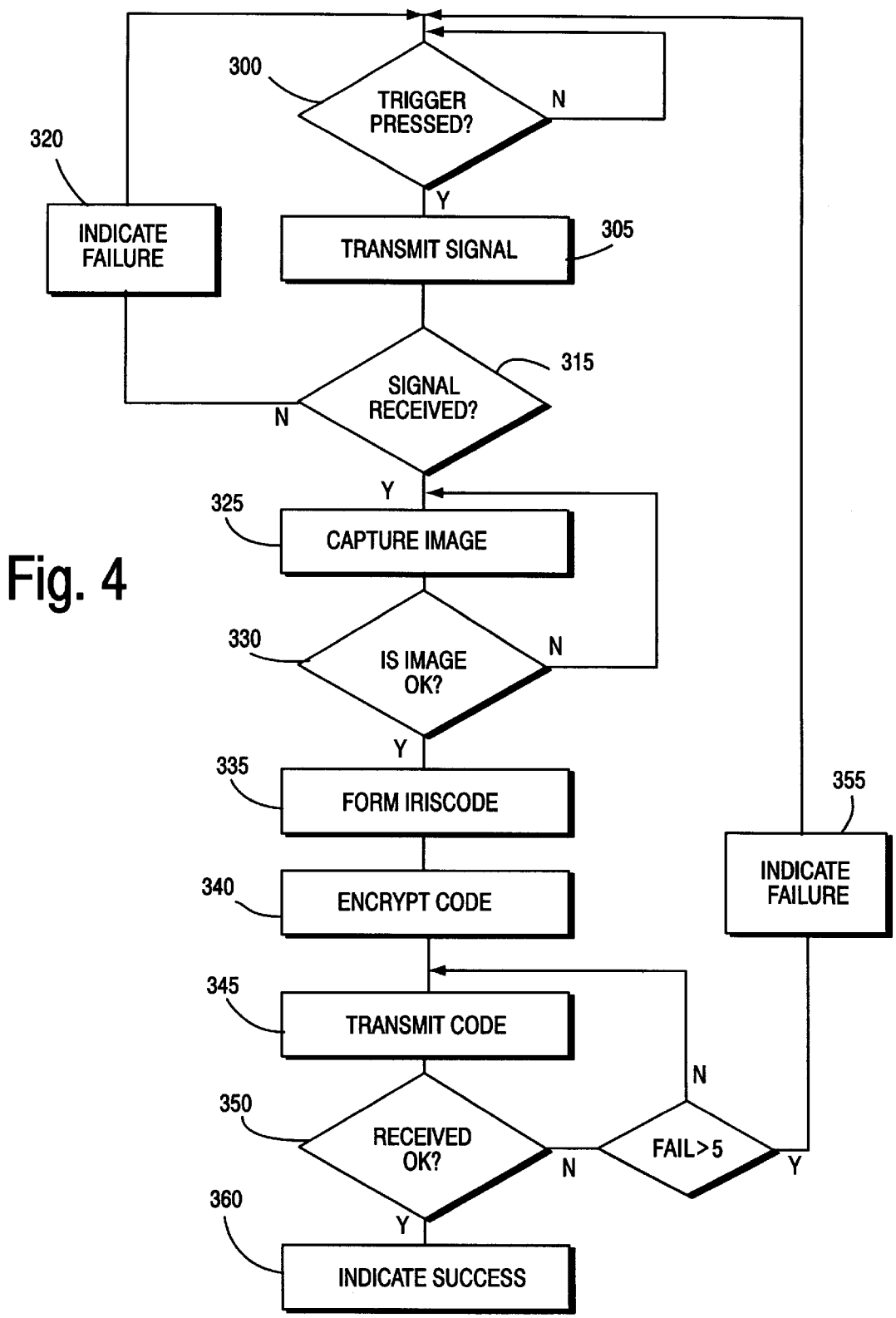
FIG. 4 is a flow chart of an image capturing and encryption process.

The flow diagram in FIG. 4 illustrates one possible process for the image capturing, processing and transmitting aspects of a user validation system. This procedure includes encryption to enhance the level of security. The encryption system uses a 'public key' to encipher data and a private key (known only to the recipient of the enciphered data) to decipher the data.

In step 300, the imaging apparatus 12 is in a state where a trigger depression is awaited to start the process. The user brings the imaging apparatus 12 to his eye and presses the trigger causing the generation a signal which is received by the processor. The processor then controls the IR transmitter 160 to send a signal, in step 305, to the user's PC 10 to initiate communications. In response, the user's PC 10 sends a return message to the imaging apparatus 12.

If the return message is not received by the imaging apparatus 12 in step 315, for example as a result of the user's PC 10 not receiving the first signal, the red LED of the optical indicator lights in step 320 to indicate failure and inform the user to re-start the process by pressing the trigger 165 again.

If the return message is received in step 315, the signal from the user's PC 10 includes a selection of which public encryption key and which iris code format the imaging apparatus 12 must use for successful transmission. A plurality of public encryption keys and a plurality of iris code algorithms from which the selection can be made are stored in the RAM (or the ROM) in the imaging apparatus 12. The user's PC 10 also transmits a date and time stamp to the imaging apparatus 12.

The information in the return signal, transmitted by the user's PC 10, is stored in the RAM in the imaging apparatus 12 for subsequent access.

Figure 5A:
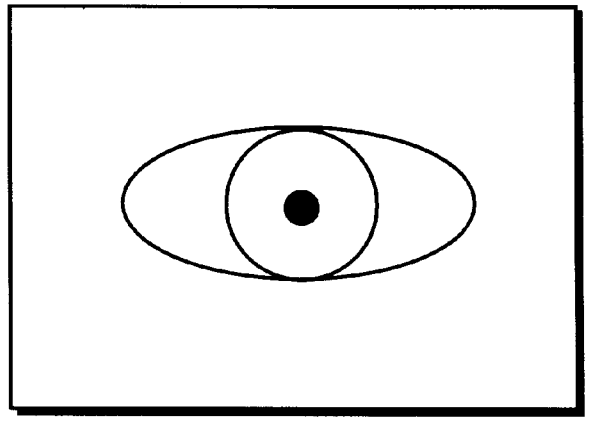
FIGS. 5a and 5b are diagrams which illustrate the display provided on the user correctly and incorrectly aligning his eye respectively.
Figure 5B:
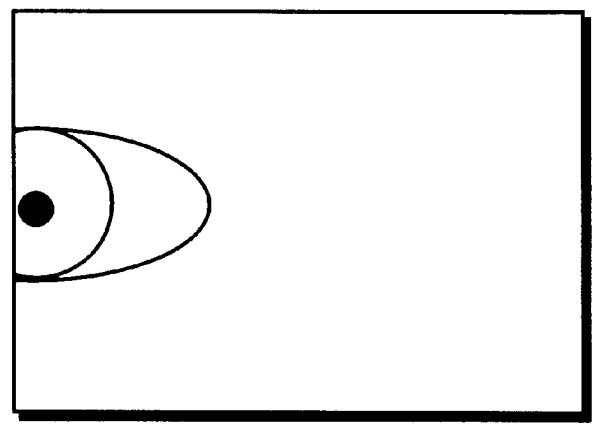

Next, in step 325, the processing means signals to the camera that one or more images should be captured. Image data captured by the CCD camera 135 is sent over the above-mentioned connection to the display 170 such that the display 170 echoes the image currently being received by the CCD camera 135. Light from the display travels along the path A through the hot mirror 145 to the user's eye 110. The light is only slightly attenuated by the mirror (approximately 90% of the visible light is transmitted. If the user's eye is correctly aligned with the window 120 then he or she sees a display like the one illustrated in FIG. 5a. If, however, the user's eye is not correctly aligned then he or she sees a display like that illustrated in FIG. 5b. The user can then change the position of his or her eye relative to the window accordingly.

The near infra-red LED 150 illuminates the user's eye 110, the light from the LED following the path B, i.e. it travels from the infra-red LED 150 to the user's iris where it is reflected towards the hot mirror 145. On reaching the hot mirror 80% of the near infra-red light is reflected by the surface coating 146 towards the CCD camera 135.

The images which are captured are stored in the RAM 215. In step 330, the processing means determines if the stored image, or which image, is suitable for encoding. If none of the one or more images is suitable, the processor signals to the camera to re-capture the image(s).

The image capturing step includes control of the near infra-red LED 150. The near infra-red LED 150 is connected in a control loop whereby the processor 200 can vary the light intensity of the source 150 depending on, for example, the colour of the user's iris: a light blue iris reflects far more light and needs less illumination than a dark brown iris. Several sequentially captured images, similar to a video sequence, might be required for the processor and software to determine the optimum illumination for the eye before a suitable image, or suitable images, is/are obtained.

It is suggested that pulsing the near infra-red LED 150 is more desirable than using a continuous source, although the image capture would need to be synchronised with a pulse of light to ensure suitable illumination. Pulsing light has the advantage that the user's eye is exposed, on average, to less optical radiation. Also, a pulsed source uses less energy.

Capturing multiple images can also overcome problems such as, for example, the user blinking at the point when one image is captured. Known digital signal processing techniques can be used to establish which image is the best and to reject unsuitable images.

When a suitable image is obtained, the image data is retrieved from the RAM 215 and is processed to form an iris code, in step 335, using the iris code generating algorithm selected by the user's PC 10 in step 315. An example algorithm is that described in U.S. pat. No. 5,291,560. The resulting iris code is stored in the RAM.

The processor 200 then encrypts the iris code, in step 340, using the selected public key, along with the date and time stamp provided by the user's PC 10 in step 315. The resulting data is stored in RAM 215. The coded and encrypted data is then transmitted to the user's PC 10 by the IR transmitter 160 in step 345.

It is feasible that the image capture, processing and encryption steps are completed without any intervening steps of storing data in RAM, that is to say processing is done "on-the-fly", to greatly increase the speed of operation of the apparatus. However, such processing would require more expensive and more complex electronics.

Finally, if the data is received successfully by the user's PC 10, the user's PC 10 returns a 'success' signal to the imaging apparatus 12 in step 350. The processing means, in response, causes the green LED of the optical indicator 185 to light to indicate to the user that the procedure has been successful in step 360. Repeated failure to transmit the data, for example after five attempts, causes the red LED of the optical indicator 185 to light in step 355 and results in the user needing to re-start the whole procedure.

A simpler process than that described above involves the imaging apparatus 12 dictating which of the plurality of public encryption keys to use. The selection can be made using a pseudo-random number generator in the imaging apparatus 12. If each public key has an index reference, the respective reference can be included, obviously in non-encrypted form, with the encrypted data to indicate to the user's PC 10 which public key has been used and, thus, which private key should be used for de-encryption. An extension to this arrangement is that a new set of public keys is down-loaded to the imaging apparatus 12, from the user's PC 10, each time a successful transaction occurs. Other, further encryption possibilities will be apparent to the skilled person.

In practice, the near infra-red LED 150 is controlled by the processor 200 (via suitable electrical circuitry which is not shown). The processor 200 controls when the infra-red LED 150 lights up to illuminate the eye, either in response to its own controlling software or in response to signals received from the user's PC 10. The processor also determines when, and under which lighting conditions, the image capturing process occurs.

As an alternative to the hot mirror used in the above embodiment, a cold-mirror may be used. The cold mirror has the same position and orientation as the hot mirror but has a different coating on its underside. The coating would be effective to reflect most visible light whilst allowing the passage of near infra-red light. The other alteration which is made in this alternative embodiment is to swap the CCD camera and the LCD display about.

It will be seen how the above described embodiments provide an optical apparatus which directs more user light towards the camera than known apparatuses. In the above embodiments this leads to the advantage that the near infra-red LED 150 need not be as bright as it would otherwise be. This means that the battery in the apparatus will last for longer and that less light will be directed towards the user's eye, making the apparatus safer to use. If the brightness of the near infra-red LED 150 is maintained at a level consistent with known apparatuses then a better image of the user's eye will be obtained. The increased light falling on the CCD camera will result in the effect of electronic noise being decreased in comparison to known apparatuses.

Although the above embodiment relates to a portable apparatus, the invention may also be applied in fixed apparatuses. For example, the optical arrangement disclosed above could be incorporated into the known System 2000EAC™ authentication apparatus. If this were done, the aperture of the optics associated with the camera in that apparatus could be stopped down, thereby increasing the depth of focus of the camera and making the apparatus easier to use.

In addition, problems associated with reflections from the user's eye of light sources other than the unit's source would be reduced. The unit's source is positioned so as to minimise reflections from the cornea of the user which tend to 'wash out' the user image. However, the human cornea is highly reflective and strongly reflects light from other sources. Usually these sources cause unwanted reflections from the cornea thereby spoiling the performance of the apparatus. By placing the above described optical system into the System 2000EAC™ apparatus the effect of visible reflections can be significantly reduced. Thus the incorporation of the above-described optical arrangement provides enhanced performance in the presence of any extraneous light sources that have some visible light within their output.

An optical arrangement similar to that described above may also be incorporated in an automated teller machine (ATM). The ATM might then require the presentation of an iris pattern matching that of an account holder before allowing the withdrawal of money from that account. Again, the present invention would be particularly useful because the increased depth of focus of the apparatus would make the ATM easier to use.

What is claimed is:

1. An apparatus for providing an information signal characteristic of an eye, said apparatus comprising:
   a housing having an entrance window;
   an illumination source mounted on the housing, and operable to illuminate the eye over an area outside the pupil; and
   an image capture device mounted within the housing, in optical communication with said entrance window, and operable to provide an image signal representing one or more features of the anterior of the eye responsive to the incidence of light from the illumination source reflected from the eye;
   an optical device;
   wherein, in use, visible light travels along a first optical path via the optical device to the eye to provide a visible image to be viewed by the eye and light from the illumination source and reflected from the eye travels along a second optical path via the optical device to said image capture apparatus;
   wherein said optical device is arranged to interact with at least one of said illumination light and said visible light such that substantially all illumination light of a pre-determined type travels further along said second optical path towards said image capture apparatus, and a significant proportion of said visible light travels further along said first optical path towards the eye.

2. An apparatus according to claim 1 wherein said visible light travels substantially unattenuated along said first optical path towards the eye.

3. An apparatus according to claim 1 further comprising a display means operable to provide at least part of said visible image.

4. An apparatus according to claim 3 wherein said display means is operable, in use, to display the image captured by the image capture apparatus.

5. An apparatus according to claim 1 wherein said pre-determined type of light differs in spectrum from said visible light.

6. An apparatus according to claim 5 wherein said optical device comprises a wavelength selective reflector effective to reflect either said visible light or said light of a different spectrum, and to allow the passage of the other.

7. An apparatus according to any preceding claim wherein said predetermined type of light substantially consists of non-visible light.

8. An apparatus according to claim 7 wherein said type of light substantially consists of near infra-red light.

9. An apparatus according to claim 8 wherein said optical device comprises a hot mirror.

10. An apparatus according to claim 1 wherein said one or more facial features comprise an iris pattern of the user.

11. An apparatus according to claim 1 wherein:
said apparatus is arranged to be carried into an operative position by a user;
said apparatus further comprises a transmission device operable to transmit said information signal derived from said image signal to a remote apparatus.

12. An optical apparatus comprising:
a user image capture apparatus operable to capture a user image of one or more facial features of a user responsive to the incidence of light reflected from the user; and
an optical device;
wherein, in use, visible light travels along a first optical path via the optical device to the user's eye to provide a visible image to be viewed by the user and user light reflected from the user travels along a second optical path via the optical device to said image capture apparatus;
wherein said optical device is arranged to interact with at least one of said user light and said visible light such that substantially all user light of a predetermined type travels further along said second optical path towards said image capture apparatus, and a significant proportion of said visible light travels further along said first optical path towards the user; and
wherein said one or more facial features comprise an iris pattern of the user.

13. An identification apparatus for providing an information signal distinctive of the iris of an individual's eye, said apparatus comprising:
a housing having an entrance window;
an illumination source mounted on the housing, and operable to illuminate the eye over an area outside the pupil; and
an image capture device mounted within the housing, in optical communication with said entrance window, and operable to provide an image signal representing one or more features of the front of the eye responsive to the incidence of light from the illumination source reflected from the eye;
a wavelength selective reflector;
wherein, in use, visible light travels along a first optical path via the wavelength selective reflector to the eye to provide a visible image to be viewed by the eye and light from the illumination source and reflected from the eye travels along a second optical path via the wavelength selective reflector to said image capture apparatus;
wherein said wavelength selective reflector is arranged to reflect one of said illumination light and said visible light such that substantially all illumination light of a predetermined spectrum travels further along said second optical path towards said image capture apparatus, and a significant proportion of said visible light of a different spectrum travels further along said first optical path towards the eye.

14. An apparatus according to claim 13, wherein said visible light travels substantially unattenuated along said first optical path towards the eye.

15. An apparatus according to claim 13 further comprising a display means operable to provide at least part of said visible image.

16. An apparatus according to claim 15 wherein said display means is operable, in use, to display the image captured by the image capture apparatus.

17. An apparatus according to claim 13 wherein said predetermined type of light substantially consists of non-visible light.

18. An apparatus according to claim 17 wherein said type of light substantially consists of near infra-red light.

19. An apparatus according to claim 18 wherein said optical device comprises a hot mirror.

20. An apparatus according to claim 13 wherein:
said apparatus is arranged to be carried into an operative position by a user;
said apparatus further comprises a transmission device operable to transmit said information signal derived from said image signal to a remote apparatus.

21. An optical apparatus comprising:
a user image capture apparatus operable to capture a user image of one or more facial features of a user responsive to the incidence of light reflected from the user; and
an optical device;
wherein, in use, visible light travels along a first optical path via the optical device to the user's eye to provide a visible image to be viewed by the user and user light reflected from the user travels along a second optical path via the optical device to said image capture apparatus;
wherein said optical device is arranged to interact with at least one of said user light and said visible light such that substantially all user light of a predetermined type travels further along said second optical path towards said image capture apparatus, and a significant proportion of said visible light travels further along said first optical path towards the user; and
wherein:
said predetermined type of light differs in spectrum from said visible light;
said optical device comprises a wavelength selective reflector effective to reflect either said visible light or said light of a different spectrum, and to allow the passage of the other; and
said one or more facial features comprise an iris pattern of the user.

* * * * *